United States Patent [19]
Baselt

[11] Patent Number: 5,981,297
[45] Date of Patent: Nov. 9, 1999

[54] BIOSENSOR USING MAGNETICALLY-DETECTED LABEL

[75] Inventor: David R. Baselt, Alexandria, Va.

[73] Assignee: The United States of America as represented by the Secretary of the Navy, Washington, D.C.

[21] Appl. No.: 08/794,979

[22] Filed: Feb. 5, 1997

[51] Int. Cl.$^6$ ............................ G01N 33/558; B01J 7/00; B03C 1/00; B01D 35/06

[52] U.S. Cl. ...................... 436/514; 422/236; 436/526; 436/528; 209/214; 210/222; 210/223

[58] Field of Search ................................. 436/514, 526, 436/528; 422/276; 209/214; 210/222, 223

[56] References Cited

U.S. PATENT DOCUMENTS

| | | | |
|---|---|---|---|
| 5,445,970 | 8/1995 | Rohr | 436/526 |
| 5,445,971 | 8/1995 | Rohr | 436/526 |

OTHER PUBLICATIONS

D.R. Baselt et al, "Biosensor Based on Force Microscope Technology", *J. Vac. Sci. Technol. B,* vol. 14, No. 2, pp. 789–793 (1996).
R. Kotitz et al. (41$^{st}$ annual conference on Magnetism and Magnetic Materials, Nov. 1996; see abstract book p. 73).
Lee et al., "Direct Measurement of the Forces Between Complimentary Strands of DNA", *Science,* vol. 266, pp. 771–773 (1994).
P. Hinterdorfer et al., "Detection and Localization of Individual Antibody–Antigen Recognition Events by Atomic Force Microscopy," *Proc. Natl. Acad. Sci. USA,* vol. 93, pp. 3477–3481 (1996).
G.U Lee et al., "Chemically Specific Probes for the Atomic Force Microscope," *Israel J. Chem.,* 36, 81–87 (1996).
M.N. Baibich et al., "Giant magnetoresistance of (001) Fe/(001) Cr magnetic superlattices", Phys. Rev. Lett., vol. 61, No. 21, pp. 2472–2475 (1988).
U.M. Daughton, "Magnetoresistive Memory Technology", *Thin Solid Films,* v. 216, pp. 162–168 (1992).
Fodor et al., Science v. 251, pp. 767–773 (1991).
Kriz et al., *Anal. Chem.* 1996, 68, 1966–1970, Jun. 1, 1996.

*Primary Examiner*—James C. Housel
*Assistant Examiner*—Rodney P. Swartz
*Attorney, Agent, or Firm*—Barry A. Edelberg

[57] ABSTRACT

This method and apparatus for detecting target molecules in a liquid phase. The apparatus monitors whether the target molecule has selectively bound to recognition agents on the surface of a magnetic field sensor by monitoring the output of the sensor. The recognition agents which selectively bind target molecules are covalently bound to microfabricated magnetic field sensors. These sensors are then exposed to a sample suspected of containing the target molecules, whereupon the recognition agents bind to and immobilize any target molecules present. Depending on the embodiment, recognition agents that selectively bind the target molecule, or recognition agents that selectively bind the sensor-bound recognition agents, are covalently bound to magnetizable particles. These particles are then added to the sensors and, again depending on the embodiment, attach either to any immobilized target molecules or to sensor-bound recognition agents. Unattached particles are removed, and the magnetic particles are then magnetized. A change in the output of the magnetic field sensors indicates the presence of magnetic particles bound to the sensors, and thereby indicates the presence and concentration of target molecule in the sample.

37 Claims, 3 Drawing Sheets

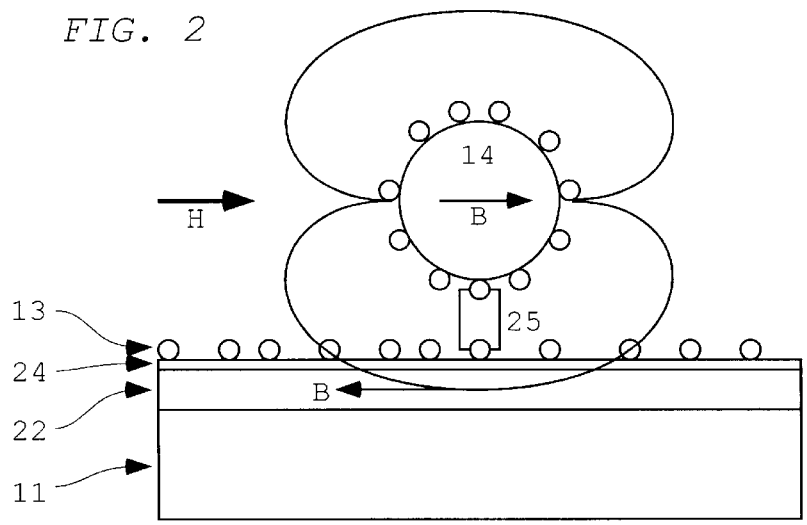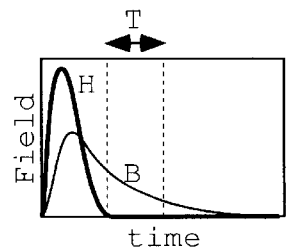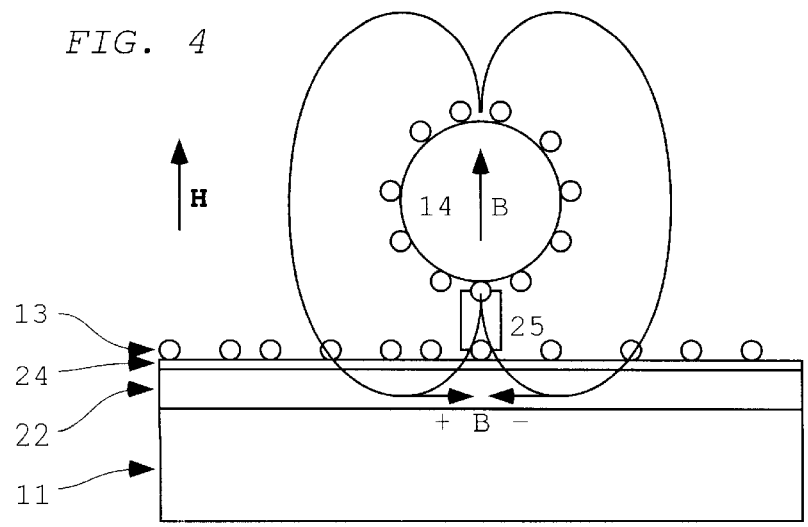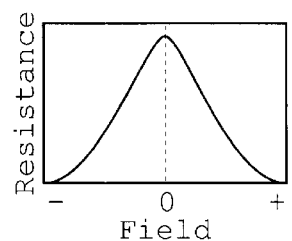

BIOSENSOR USING MAGNETICALLY-DETECTED LABEL

BACKGROUND OF THE INVENTION

1. Field of the Invention

The present invention relates to a method and apparatus for detecting target molecules with binding assays, such as DNA, RNA, receptor, or antibody binding assays, taking advantage of labels that produce and respond to magnetic fields.

2. Description of the Previously Published Art

Binding assays such as immunoassays, DNA hybridization assays, and receptor-based assays are widely used in the medical community as diagnostic tests for a wide range of target molecules.

As used herein, the term "analyte" indicates the molecule, species, or organism whose presence, absence, or concentration one is interested in determining, while the term "target molecule" or "target species" indicates the molecular species whose presence, absence, or concentration the assay in question actually determines. The target and analyte may be identical, or the target may be indicative of the presence or absence of the analyte. In particular, target molecules such as proteins or DNA may be a distinctive component or product of analytes such as viruses, bacteria, or other organisms, and therefore indicative of their presence.

Binding assays exploit the ability of certain molecules, herein referred to as "binding molecules", to specifically bind target molecules. Binding molecules such as antibodies, strands of polynucleic acids (DNA or RNA) and molecular receptors, are capable of selectively binding to ("recognizing") such potential target molecules as polynucleic acids, enzymes and other proteins, polymers, metal ions, and low molecular weight organic species such as toxins, illicit drugs, and explosives.

In a solid-phase binding assay, binding molecules are attached to a solid substrate, a procedure generally performed by the manufacturer of the assay. These binding molecules are referred to as "capture" molecules. When the user initiates the assay by exposing the solid substrate to a liquid sample, capture molecules immobilize target and/or label molecules on the surface via recognition events.

Through the use of labeled binding molecules, such recognition events can be made to generate a measurable signal and therefore indicate the presence or absence of a target molecule. Various types of binding assays have been devised that use radioactive, fluorescent, chemiluminescent, or enzymatic labels. Depending on the type of assay being performed, labeled binding molecules either bind to immobilized target molecules ("sandwich" assay), or compete with target molecules to bind to capture molecules ("competitive" assay). After removal of excess label, the amount of bound label is measured.

A large number of variations on the above-described binding assay methodologies have been described. For a more complete description, see a laboratory handbook such as P. Tijssen, Practice and Theory of Enzyme Immunoassays, Elsevier Science Publishers, Amsterdam, 1985, the entire contents of which are incorporated herein by reference. The common feature of all binding assays is that labeled binding molecules adhere to a solid substrate in numbers that reflect the concentration of the target molecule.

Nonspecific binding of the label, i.e. label adhering to the substrate by means other than recognition events (such as charge-charge interactions, van der Waals interactions, or adhesive contamination), is an important factor that limits the sensitivity of binding assays.

Several binding assays have been described that use magnetic particles as labels. The Force Amplified Biological Sensor (FABS) described in "Biosensor Based on Force Microscope Technology", by D. R. Baselt, G. U Lee, and R. J. Colton, J. Vac. Sci. Technol. B, vol. 14, no. 2, pp. 789–793, (1996); and in U.S. patent application Ser. No. 08/505,628, filed Jul. 21, 1995, by G. U Lee, R. J. Colton, and D. Kidwell uses a cantilever-beam force transducer to measure the total magnetic force exerted by adhering label when a magnetic field is applied.

A device described by T. Rohr in U.S. Pat. Nos. 5,445,970 and 5,445,971 uses a microbalance, rather than a cantilever-beam force transducer, to measure the force exerted by adhering magnetic label when a magnetic field is applied.

A binding assay described by R. Kotitz et al. ($41^{st}$ annual conference on Magnetism and Magnetic Materials, Nov. 1996; see abstract book p. 73) uses a Superconducting Quantum Interference Device (SQUID) to detect whether magnetic particles have been immobilized by biological recognition events on the side of a test tube.

The atomic force microscope (AFM) has been used by a number of research groups to measure the forces associated with recognition events. Typically, a binding molecule is attached to an AFM force transducer and a capture molecule is attached to a solid surface (or vice-versa), and the AFM is used to pull the two apart. See for example Lee et al., "Direct Measurement of the Forces Between Complimentary Strands of DNA", Science vol. 266, pp. 771–773 (1994); Hinterdorfer et al., "Detection and Localization of Individual Antibody-Antigen Recognition Events by Atomic Force Microscopy," Proc. Natl. Acad. Sci. USA vol. 93, pp. 3477–3481 (1996). In effect, such experiments detect the presence of a target molecule and discriminate specific from nonspecific interactions ("force discrimination"). Force discrimination requires that binding molecules be securely attached (i.e. covalently bonded) to the substrate and to the magnetic label. Substrate attachment is presently performed by a procedure described by G. U Lee et al., "Chemically Specific Probes for the Atomic Force Microscope," Israel J. Chem. 36, 81–87 (1996). More significantly for research purposes, such experiments could make it possible to better understand the physical basis and behavior of recognition events. In principle, it should be possible to perform the same type of study using magnetically-attracted particles rather than an AFM to pull bonds apart.

The magnetic labels generally used for FABS are beads or particles made either from nanometer-sized iron oxide crystallites, polymer impregnated with nanometer-sized iron oxide crystallites, or porous glass filled with iron oxide crystallites. Such particles are commonly used for magnetic separation in molecular biology and are manufactured by several firms, including Dynal, Inc., Lake Success, N.Y.; Bangs Laboratories, Inc., Carmel, IN; CPG, Inc., Lincoln Park, N.J.; and PerSeptive Biosystems, Framingham, Mass. These particles can be obtained with surface functional groups that may be used to immobilize molecules such as streptavidin, antibodies, or DNA. The particles are paramagnetic; that is, their magnetization is a function of the external magnetic field, and when the field is removed, the magnetization of the particles settles to zero. This "relaxation" does not happen instantly, but occurs over a period typically measured in microseconds or milliseconds, depending on the size of the iron oxide crystallites. Particles based on nanometer-sized iron oxide crystallites are sometimes termed "superparamagnetic", since their magnetization in a given magnetic field tends to be much greater than normal paramagnetic materials.

Particles fabricated from ferromagnetic materials (such as NdFeB or nickel) or ferrimagnetic materials (such as micron-sized iron oxide or ferrite particles) can also be used as magnetic labels. Both types of materials can be magnetized to a substantially greater magnetic moment than superparamagnetic particles, but they also retain their magnetism in the absence of an external magnetic field. Since magnetized particles aggregate and thus cannot be used in a FABS assay, the particles must be obtained in a nonmagnetic state and kept nonmagnetic until they are immobilized by the antibody-antigen interactions. These materials therefore present certain development challenges.

3. Objects of the Invention

It is an object of this invention to selectively detect a wide range of chemical and biological species obtained from either the vapor or liquid phase, with a high degree of sensitivity.

It is a further object of this invention to simultaneously detect numerous chemical or biological species in a single assay.

It is a further object of this invention to rapidly detect chemical and biological species, on the order of 15–30 minutes per assay.

It is a further object of this invention to produce a sensor for chemical and biological species in the form of a compact, fully automated device.

It is a further object of this invention to measure intermolecular binding forces and thereby analyze recognition events.

These and further objects of the invention will become apparent as the description of the invention proceeds.

SUMMARY OF THE INVENTION

A new method and apparatus for detecting the presence, absence, or concentration of one or more target molecular species in a sample suspected of including the target species has been developed using a magnetic field detector. The detector has one or more magnetic field sensors. Closely bound to the sensors are binding molecules which are capable of binding to the target molecules. The sample and one or more species of magnetizable label particles are brought into contact with the detector at the same or at different times. These label particles have attached binding molecules that specifically bind to either the target species, the sensor-bound binding molecules, or both the target species and the sensor-bound binding molecules. As a result, label particles bind close to the sensors in numbers that relate to the concentration of the target species. The unbound label particles are removed and the remaining bound label particles are magnetized. The output of a magnetic field detector is monitored to detect the magnetic field produced by the magnetized label particles so as to determine the number of bound magnetic particles and thereby the concentration of the target molecule is determined.

The preferred magnetizable label particles are superparamagnetic iron oxide-impregnated polymer beads and the preferred magnetic field sensor is a magnetoresistive material. By patterning a magnetoresistive film when making the sensor an array can be made. If each magnetic field sensor is of a small size it can detect the presence or absence of label particles with single-particle sensitivity. The detector can provide a digital binary value to indicate whether or not a label particle is present. The unbound label particles can be removed by applying a magnetic force to the particles. Examples of the binding molecules are antibodies; poly- or oligo- nucleotides, i.e. DNA or RNA; proteins; synthetic polypeptides; and chelators. Exemplary target molecules include polynucleic acids, proteins, metal ions, and low molecular weight organic species such as toxins, illicit drugs, and explosives.

An especially preferred method for contacting the sample with the sensor is to place the sample in a solution which is applied to the detector. Then a second solution containing one or more species of magnetizable label particles is applied to the detector where the particles have attached label-bound binding molecules with a selective binding response to the target molecules. In the presence of target molecules which have been bound to the sensor, these label-bound binding molecules will sandwich target molecule to form a link between the magnetizable label particle and the sensor.

The apparatus for carrying out the method has one or more magnetic field sensors which have closely attached binding molecules capable of undergoing a selective binding interaction with the target molecular species. Magnetizable label particles are used having binding molecules capable of undergoing a selective binding interaction with either the target molecular species or the sensor bound binding molecules so that the label particles are attached to the magnetic field sensors. Magnetizing means are provided for magnetizing the attached label particles and detection means are used for monitoring the magnetic field sensors so as to detect the magnetic field produced by the presence of the attached magnetized label particles and thus the concentration of the target molecule is determined.

The invention has a projected sensitivity several orders of magnitude greater than established techniques and, at 15–30 minutes per assay, is expected to operate much faster. It is expected to take the form of a compact, fully automated device. It is compatible with microfabrication technology, and could therefore be implemented as a multiple-sensor array capable of performing several assays simultaneously. These large-array applications are potentially very valuable in applications such as combinatorial screening and test batteries. It is also expected to be capable of measuring intermolecular binding forces and thereby analyzing recognition events.

BRIEF DESCRIPTION OF THE DRAWINGS

FIG. 2 illustrates a magnetic particle bound to an element of magnetoresistive material by biomolecular recognition interactions, and magnetized for relaxation-mode detection.

FIG. 3 is a graph which schematically illustrates the decay of the magnetic particle magnetization B after the external field H is removed.

FIG. 4 illustrates a magnetic particle bound to an element of magnetoresistive material by biomolecular recognition interactions, and magnetized for scissoring-mode detection.

FIG. 5 is a graph which schematically illustrates the symmetric response of the magnetoresistive element to magnetic fields parallel to the plane of the element.

DESCRIPTION AND OPERATION OF THE PREFERRED EMBODIMENTS

Figure 1:
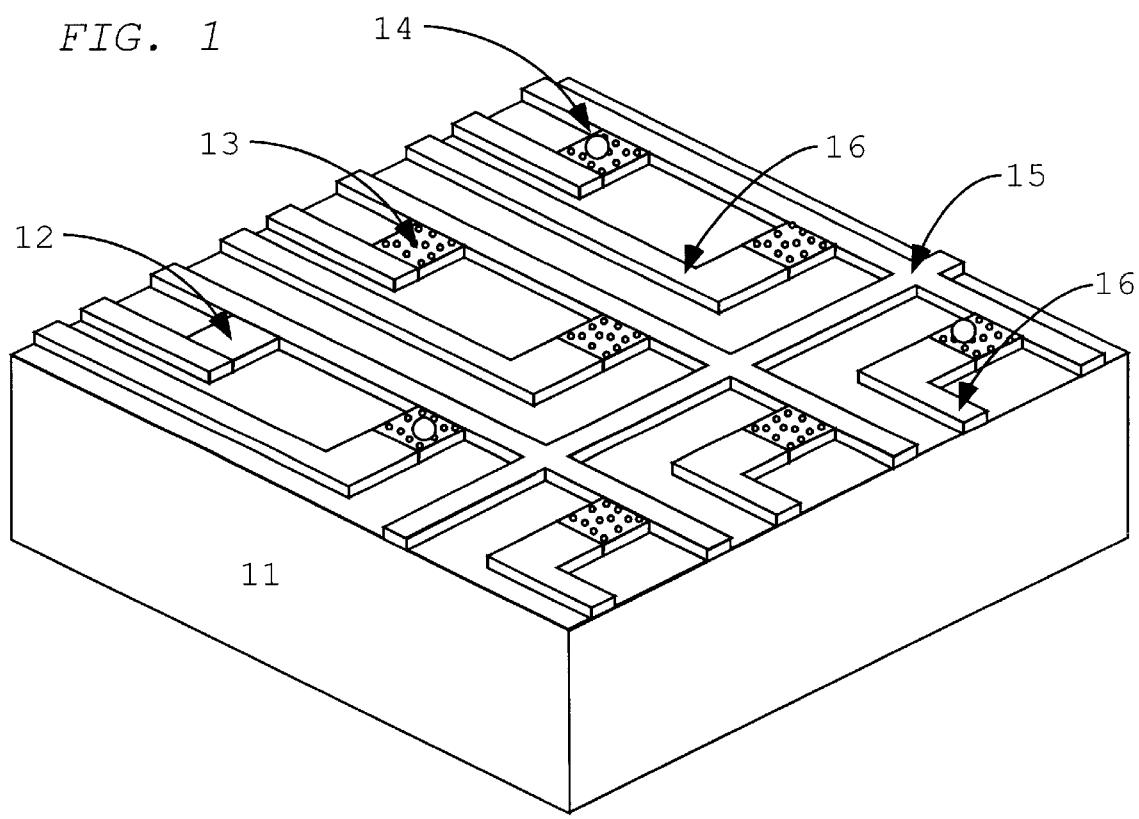
FIG. 1 illustrates a portion of an array of magnetoresistive sensing elements for use in the first embodiment of the invention.

The present invention resembles FABS in that both are highly-sensitive binding assays that use magnetic label. In the present invention, however, the magnetic field, rather than the force, generated by the magnetic label is detected. This detection is accomplished with a magnetic field sensor located within several microns of the magnetic label. Recent developments in magnetoresistive materials have made it possible to microfabricate such detectors and make them of high sensitivity and micrometer-scale size. The preferred embodiments of the present invention take advantage of these capabilities.

Magnetoresistive materials are generally composite metals; their electrical resistance is a function of the angle between their magnetic polarization and the flow of electric current. See for example M. N. Baibich et al., "Giant magnetoresistance of (001)Fe/(001) Cr magnetic superlattices", Phys. Rev. Lett. vol. 61 no. 21, pp. 2472–2475 (1988). Among other applications, magnetoresistive sensors are used for reading magnetic tapes or disks, for hand-held magnetic field sensors, and for computer memory chips.

In its preferred embodiment, the present invention takes the form of a small desktop unit into which the user injects about 100 µl of a liquid sample, or, alternatively, a miniaturized handheld or remote unit connected to an environmental (air, water, sewage, etc.) sampler. Within the unit is a disposable, but multiuse, liquid flow cell through which the sample flows. The cell contains a "detector", which is a microfabricated device bearing magnetoresistive elements.

Using microlithography, it is possible to make arrays of thousands or even millions of tiny (micron-sized) magnetoresistive sensing elements on a single 1×1 cm detector. Such arrays have three advantages.

First, while the sensitivity of FABS cantilevers is reduced if the cantilever is shortened, the sensitivity of magnetoresistive elements improves if the element size is decreased toward the dimensions of a single magnetic labeling particle. Thus, small magnetoresistive elements provide optimal sensitivity to magnetic beads. High sensitivity allows the use of simple, inexpensive detection electronics, allows smaller magnetic particles to be sensed, and enables detection within a short period of time, such as microseconds or milliseconds. A short detection time is needed for "relaxation" mode detection as will be described below. Small magnetic particles are advantageous because they diffuse faster and thus speed the kinetics of the immunoassay; additionally, they experience less drag as a solution flows by them, and thus are not as likely as large particles to become detached from the sensor as solutions are passed through the flow cell.

Second, each element can be designed to detect only one labeling particle. A one-particle-per-element embodiment would preferably contain thousands or millions of very small magnetoresistive sensing elements. Appropriate electronic circuitry, either external to the detector or buried under the magnetoresistive elements, can provide a binary signal that is compatible with digital electronics and that indicates whether or not a labeling particle is present above a given element. The one-particle-per-element configuration would offer an accurate count of bound particles even if the signal-per-particle level varied widely between particles. Such variation might result from variations in particle volume, particle magnetic properties, particle aggregation, or magnetoresistive element sensitivity.

Third, different magnetoresistive elements can be coated with different antibodies, potentially allowing thousands of target species to be sensed simultaneously. Note, however, that the sensitivity of a binding assay is proportional to the active area of the detector. This active area is defined as the total area coated with a binding molecule against a particular target species. If the active area is doubled, the odds of capturing a target molecule are correspondingly doubled. Thus, while a one-particle-per-element configuration provides optimal magnetic sensitivity, a one-element-per-target configuration would provide poor chemical sensitivity unless the elements were very large. Each target species will therefore be detected by a group of 1000 or more elements, depending on the desired sensitivity.

On the other hand, the one-particle-per-element configuration results in a more elaborate and expensive detector. Thus two embodiments of the detector are presented. The first does not use the one-particle-per-element configuration, while the second does.

In comparison with previously-described sensors that use magnetizable label, the present invention is considerably simpler, and therefore less expensive, to construct. FABS, for example, uses piezoresistive cantilevers sandwiched between two micromachined electromagnet coils. The equivalent component of the present invention has only one part, which is the "detector" to be described below, with relatively simple microfabrication requirements.

FIG. 1 illustrates a portion of a many-particle-per-element detector. The magnetoresistive elements measure approximately 20×20 µm and are fabricated by photolithography (or by some other form of microlithography) of a magnetoresistive film deposited on a silicon wafer 11. Reference magnetoresistive elements such as 12 do not bear binding molecules. Signal magnetoresistive elements bear a coating of covalently-attached binding molecules 13, depicted by the small circles. The signal magnetoresistive element 14 has a magnetic particle attached via a recognition event. To simplify FIG. 1, neither the binding molecules on the particles nor the target molecules are shown. A network of microfabricated gold strips 15 carries the bias voltage. Separate microfabricated gold strips such as 16 carry the output voltage. The detector has one output strip for each magnetoresistive element. A thin coating of siliconoxynitride, polymer, diamond-like carbon, or other insulating material covering the magnetoresistive elements and the gold strips 15 and 16 is not shown. The binding molecule coating 13 is applied over the insulating material. The entire detector, containing some 250 magnetoresistive elements, measures approximately 1×1 and is capable of detecting 10 target species.

The preferred binding assay is a sandwich immunoassay, and the binding molecules are therefore antibodies. This procedure is illustrated in Baselt et al., "Biosensor Based on Force Microscope Technology", J. Vac. Sci. Technol. B vol 14, no. 2, pp. 789–793 (1996) the entire contents of which are incorporated herein by reference. Antibodies, covalently attached to the insulating coating over the magnetoresistive elements, will bind to and immobilize target molecules present in the sample solution. Next, a suspension of 1–5 µm diameter superparamagnetic beads is introduced into the liquid cell. Like the magnetoresistive elements, these labeling beads bear covalently-attached antibodies that adhere to the immobilized target molecules.

Thus, as a result of this immunoassay, superparamagnetic particles adhere to magnetoresistive sensing elements by antibody-antigen bonds. The purpose of the detector is to count the number of adhering particles, which is proportional to the concentration of analyte in the sample.

Before the detector is activated, though, a magnetic device, preferably an electromagnet, is used to remove nonspecifically-adhering particles. The magnetic fields required for this purpose are large, and, to avoid the requirement of correspondingly large and heavy instrumentation, would be best provided by sending a brief (~10–100 ms) pulse of current, generated by a capacitive-discharge circuit, through an air-core electromagnet coil.

Thus, in a preferred embodiment, an air-cored electromagnet measuring 0.5 inch in diameter and containing approximately 2000 turns of 0.005 inch diameter wire is located 0.13 inch above the detector. A 6 ampere pulse of current is applied to the electromagnet, producing a force of approximately 25 pN on each superparamagnetic particle for 10 ms.

The detector operates as follows. A magnetic field generator creates a magnetic field that magnetizes the beads. The magnetic field generator can be an electromagnet, an air-cored wire coil, a straight wire, a conductive microfabricated trace, or a permanent magnet. Each magnetized bead generates a magnetic field that changes the resistance of the magnetoresistive element to which it is bound. A Wheatstone bridge is used to compare the resistance of the signal element with that of a reference element, which is located near the signal element and is identical to it, except that it lacks antibodies. The output of the Wheatstone bridge is converted to digital form; a microprocessor collects the resulting information and determines the total number of magnetized beads on the detector. From this information, and calibration data provided by the manufacturer of the device, the microprocessor can calculate the target species concentration.

If proper measures are not taken, the field generated by the electromagnet will also affect the magnetoresistive element and overwhelm the relatively small magnetic fields generated by the beads. Three possible ways to avoid this problem are as follows.

First, the electromagnet can be turned off and the magnetization of the beads measured before it decays to zero. This detection strategy is herein referred to as "relaxation mode". FIG. 2 illustrates a labeling particle bound to a magnetoresistive element by sandwich-mode binding chemistry, and magnetized for relaxation-mode detection. The figure is not to scale. The substrate 11 bears the magnetoresistive element 22, which is covered with insulating material 24 and a coating of binding molecules 13. An external magnetic field of about 100 Oe, indicated by the arrow labeled "H", magnetizes the magnetic particle 14 parallel to the magnetoresistive element. The particle is attached to the magnetoresistive element via the target molecule 25. It produces a magnetic field of about 10 G in the plane of the magnetoresistive element, as indicated by the arrow labeled "B", thereby altering the resistance of the element. FIG. 3 is a graph that schematically depicts the decay of the magnetic particle magnetization B after the external field H is switched off. The magnetoresistive element detects the decaying field during the time T, thereby avoiding interference from the external field H.

Second, the electromagnet can be located to produce a field oriented perpendicular to the magnetoresistive element. The magnetoresistive element will not detect such a field, but it will detect the field generated by the bead in response. This detection strategy is herein referred to as "scissoring mode". FIG. 4 illustrates a magnetic particle 14 bound to an element of magnetoresistive material 22 by sandwich-mode binding chemistry, and magnetized for scissoring-mode detection. The figure is not to scale. The substrate 11 bears the magnetoresistive element 22, which bears a layer of insulating material 24 and a coating of binding molecules 13. An external magnetic field of about 100 Oe, indicated by the arrow labeled "H", magnetizes the magnetic particle 14 perpendicular to the magnetoresistive element. The particle, attached to the magnetoresistive element via the target molecule 25, produces positive and negative magnetic fields of about 10 G in the plane of the magnetoresistive element, as indicated by the two arrows labeled "B". Interference from the external field H is avoided because the magnetoresistive element 22 is insensitive to fields perpendicular to the plane of the element. FIG. 5 is a graph that schematically illustrates the response of the magnetoresistive element to magnetic fields parallel to the plane of the element. Because the response is insensitive to the sign of the magnetic field B, the positive and negative fields generated by the magnetic particle 14 do not cancel out, but produce a net resistance change in the magnetoresistive element 22.

Third, the superparamagnetic bead can be replaced with a ferromagnetic bead. The electromagnet can then be turned off and the remanent magnetization of the beads measured.

Devices containing millions of micron-sized, individually-addressable magnetoresistive sensors with digital readout have been proposed for use in computer memories. These devices are referred to as "Magnetoresistive RAM" or MRAM, and each magnetoresistive sensor is actually a single storage bit. See for example J. M. Daughton, "Magnetoresistive Memory Technology", Thin Solid Films v. 216, pp. 162–168, (1992).

Figure 6:
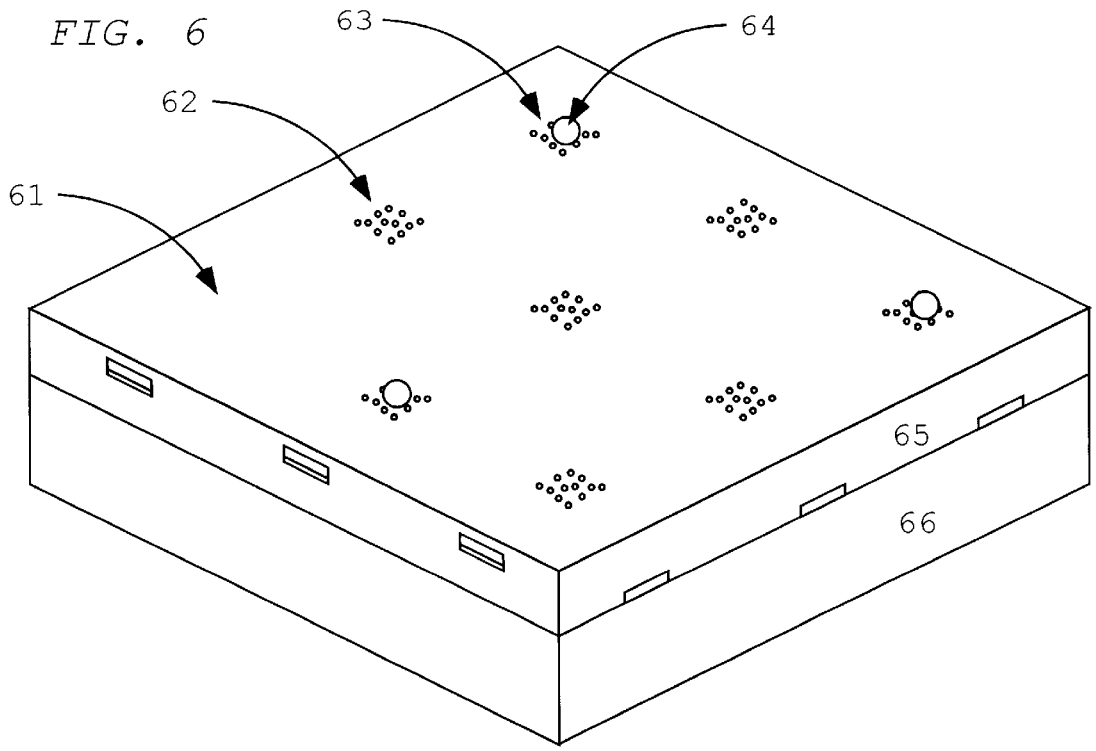
FIG. 6 illustrates a portion of an array of magnetoresistive sensing elements for use in the second embodiment of the invention.

FIG. 6 illustrates a portion of a one-particle-per-element detector. The sensing elements are buried within the device and are not visible. The detector has reference detection regions, such as 61, that do not bear binding elements. In contrast, signal detection regions, such as 62, have a coating of binding elements as shown by the small circles. The detection region 63 has a magnetic particle 64 attached via a recognition event. To simply FIG. 6, the drawing shows neither the binding elements on the magnetic particle nor the target molecule. The insulating layer 65 protects the sensing elements from sample solutions; its surface has been made flat by float-polishing. The entire unit is fabricated on a silicon substrate 66.

Figure 7:
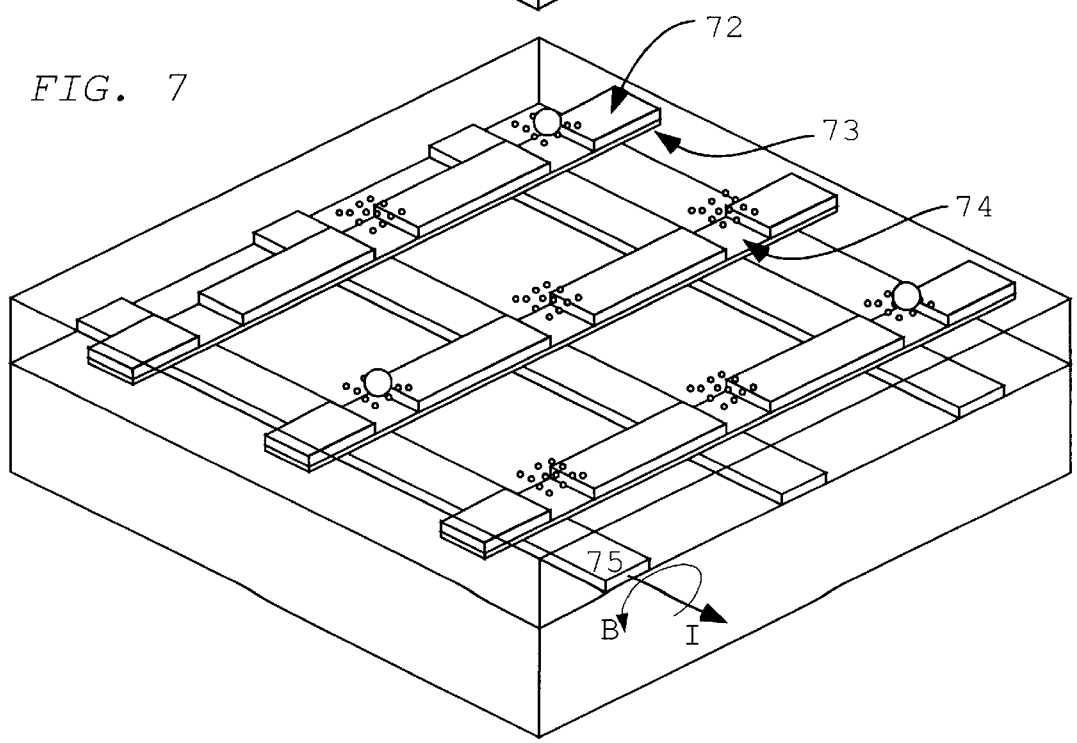
FIG. 7 illustrates a portion of an array of magnetoresistive sensing elements, for use in the second embodiment of the invention, where the insulating layer has been rendered transparent to reveal the sensing elements.

FIG. 7 illustrates a portion of a detector as shown in FIG. 6, but the insulating layer has been rendered transparent to reveal the sensing elements. Rectangles of shorting metal 72 are microfabricated on strips of magnetoresistive material 73 to define the sensing elements 74, which are the areas of the magnetoresistive strips 73 not covered with shorting metal 72. Each magnetoresistive strip 73 has approximately 5 sensing elements 74. Running underneath and at right angles (and not electrically connected) to the magnetoresistive strips 73 are microfabricated metal lines 75. Current indicated by the arrow labeled "I" in FIG. 7 can be made to flow in these metal lines 75 and thereby generate a magnetic field parallel to the magnetoresistive strips 73, indicated by the arrow labeled "B" in FIG. 7. In response, superparamagnetic particles such as 64 bound above the sensor pads generate a magnetic field parallel to the magnetoresistive strips. This magnetic field is detected with relaxation-mode detection. The current flowing through the metal lines is turned off and, in the following microseconds, the sensing elements measure the decaying magnetic field generated by the superparamagnetic particle, if one is present.

An example of a prototype detector, implemented as illustrated in FIG. 1 or FIG. 7, has each sensor element 12 or 74 with an active area of 3×3 μm. Elements are separated by 6 μm to prevent crosstalk. A 64×64 array of these sensor elements forms a sensor cluster responsible for detecting one species of target molecule. Sensor clusters are separated by 360 μm to allow for the limited resolution of the binding molecule patterning process. The complete detector chip will be a 10×10 array of clusters measuring 1×1 cm, containing 400,000 sensor elements and capable of detecting 100 different target species.

This detector could be expanded to 1000 target species by increasing chip size to 1.6×1.6 cm and cutting the spacing of sensor elements and clusters in half.

Detecting 100 different target species will require attaching 100 different binding molecule species to the magnetoresistive array. Attaching each type of binding molecule sequentially would result in an impractical 100-cycle procedure. A more practical approach would involve conjugating the binding molecules to DNA tags, with each type of binding molecule having a unique tag. Combinatorial array synthesis techniques, such as those described by Fodor et al., Science v. 251, pp. 767–773 (1991) can then be used to produce complimentary DNA tags on the magnetoresistive array. A DNA tag having n bases will support $2^n$ different types of binding molecule; i.e., a 100-analyte array will require 7-base-pair tags, while a 1000-analyte array will require 10-bp-tags. Thus, following a 7-cycle synthesis, all the antibodies can be attached simultaneously via a hybridization reaction.

To more strongly attach binding molecules to the substrate, an unchanging leader of perhaps 13 base pairs can be added to the 7 bp tags. This would result in a 20 bp DNA—DNA binding interaction, which should be about 4 times stronger than an antibody-antigen interaction and should not break while force discrimination is carried out.

Other magnetic field sensors, such as a magnetostrictive film, could perform the same task as the magnetoresistive film described above. Furthermore, the binding assay used in the present invention is not limited to antibody-based detection. Any selective binding agent can attach the beads to the analyte and the analyte to the detector. DNA, antibiotics, receptor proteins, synthetic polypeptides, and synthetic oligopeptides are possible examples.

The preferred binding mode for the magnetizable particles to the bound target molecules in the sample is the sandwich mode described above. Other binding modes can be used. For example, the competitive mode can be used where magnetizable label particles have attached label-bound binding molecules with a selective binding response to sensor-bound binding molecules. The sample solution is applied along with one or more species of the magnetizable label particles and as a result the target molecules and the label particles compete for binding to the sensor. Again the amount of label particles that ultimately bind will be a function of the concentration of the target molecules.

Another binding mode is the dissociative mode in which the sensor is first contacted with a solution containing one or more species of magnetizable label particles having attached label-bound binding molecules with a selective binding response to the sensor-bound binding molecules. These label particles bind to the sensor and then the sample solution is applied and the target molecules displace the bound magnetizable label particles and the target molecules bind to the sensor-bound binding molecules. Again the amount of label particles that ultimately remain bound will be a function of the concentration of the target molecules.

It is understood that the foregoing detailed description is given merely by way of illustration and that many variations may be made therein without departing from the spirit of this invention.

What is claimed is:

1. An apparatus for detecting a target molecular species, comprising:
   a magnetoresistive or magnetostrictive magnetic field sensor having attached thereto binding molecules which selectively bind the target molecular species;
   magnetizable label particles bearing binding molecules which:
      (1) selectively bind the target molecular species or, in the alternative,
      (2) selectively bind the sensor bound binding molecules, and
         (i) compete for said selective binding of said sensor bound binding molecules with said selective binding of said target molecular species to said sensor bound binding molecules, or
         (ii) are displaced from said sensor bound binding molecules by said selective binding of said target molecular species to said sensor bound binding molecules,
   whereby the label particles attach to the magnetic field sensor as a result of said selective binding;
   magnetizing means for magnetizing the attached label particles; and
   detection means for monitoring a magnetoresistive or magnetostrictive response of the magnetic field sensor to a magnetic field produced by one or more magnetized label particles attached to said magnetic field sensor, whereby the concentration of the target molecule is determined.

2. An apparatus according to claim 1, wherein the magnetizable label comprises one or more materials selected from the group consisting of paramagnetic, superparamagnetic, ferromagnetic, and ferrimagnetic materials.

3. An apparatus according to claim 2, wherein the magnetizable label comprises superparamagnetic, iron oxide-impregnated polymer beads.

4. An apparatus according to claim 1, wherein the magnetic field sensor comprises a magnetoresistive material.

5. An apparatus according to claim 4, wherein the magnetoresistive material is anisotropic magnetoresistive; giant magnetoresistive; or colossal magnetoresistive.

6. An apparatus according to claim 1, wherein the magnetic field sensor is magnetostrictive.

7. An apparatus according to claim 1, wherein the magnetic field sensor is a magnetoresistive element made by patterning a magnetoresistive film.

8. An apparatus according to claim 7, wherein the patterning of the magnetoresistive film is accomplished using photolithographic or other microlithographic patterning.

9. An apparatus according to claim 1, wherein there are a plurality of magnetic field sensors.

10. An apparatus according to claim 9, wherein each magnetic field sensor detects the presence or absence of a single label particle attached to said magnetic field sensor.

11. An apparatus according to claim 10, wherein said detection means provides a digital binary value indicating whether or not a label particle is present.

12. An apparatus according to claim 1, further comprising means to add the target molecules and the magnetizable particles to the sensor.

13. An apparatus according to claim 1, wherein the magnetizing means is a magnetic field generator and preferably a wire coil, a straight wire, a conductive microfabricated trace, or a permanent magnet.

14. An apparatus according to claim 1, further comprising means to remove nonspecifically-bound label particles.

15. An apparatus according to claim 14, wherein the nonspecifically-bound label particles are removed by a means for applying a magnetic force to the particles and preferably an electromagnet, an air-cored coil, or a permanent magnet.

16. An apparatus according to claim 15, wherein the means to apply the magnetic force is the magnetizing means for magnetizing the label particles.

17. An apparatus according to claim 1, wherein the binding molecules are antibodies; poly- or oligo-nucleotides, i.e. DNA or RNA; proteins; synthetic polypeptides; or chelators.

18. An apparatus according to claim 1, wherein the target molecules are selected from the group consisting of polynucleic acids, proteins, metal ions, and low molecular weight organic species such as toxins, illicit drugs, and explosives.

19. An apparatus according to claim 1, wherein the detection means comprises a Wheatstone bridge for monitoring both a magnetic field sensor having closely-attached binding elements and an identical field sensor without binding elements.

20. A method for detecting the presence of a target molecular species in a sample suspected of including said target species, comprising the steps of:

a) providing a detector comprising a magnetoresistive or magnetostrictive magnetic field sensor having binding molecules which selectively bind to the target molecules and which are bound to the sensor;

b) bringing the sample and one or more species of magnetizable label particles into contact with the detector at the same or at different times, said label particles having attached binding molecules that;

(1) selectively bind the target species, or, in the alternative;

(2) selectively bind the sensor-bound binding molecules, and (i) compete for said selective binding of said sensor-bound binding molecules with said selective binding of said target molecular species to said sensor-bound binding molecules, or (ii) are displaced from said sensor-bound binding molecules by said selective binding of said target molecular species to said sensor-bound binding molecules, whereby said label particles attach to the sensor as a result of said selective binding, the number of said label particles attached to said sensor being related to the concentration of the target species;

c) removing unbound label particles;

d) magnetizing the remaining bound label particles; and e) monitoring a magnetoresistive or magnetostrictive response of said magnetic field detector to a magnetic field produced by one or more magnetized label particle attached to said magnetic field sensor, whereby the concentration of the target molecule is determined.

21. A method according to claim 20, wherein the magnetizable label comprises one or more materials selected from the group consisting of paramagnetic, superparamagnetic, ferromagnetic, and ferrimagnetic materials.

22. A method according to claim 21, wherein the magnetizable label comprises superparamagnetic iron oxide-impregnated polymer beads.

23. A method according to claim 20, wherein the magnetic field sensor comprises a magnetoresistive material.

24. A method according to claim 23, wherein the magnetoresistive material is anisotropic magnetoresistive; giant magnetoresistive; or colossal magnetoresistive.

25. A method according to claim 20, wherein the magnetic field sensor is magnetostrictive.

26. A method according to claim 20, wherein the magnetic field sensor is a magnetoresistive element made by patterning a magnetoresistive film.

27. A method according to claim 26, wherein the patterning of the magnetoresistive film is accomplished using photolithographic or other microlithographic patterning.

28. A method according to claim 20, wherein there are a plurality of magnetic field sensors.

29. A method according to claim 28, wherein each magnetic field sensor detects the presence or absence of a single label particle attached to said magnetic field sensor.

30. A method according to claim 29, wherein said detection means provides a digital binary value indicating whether or not a label particle is present.

31. A method according to claim 20, wherein the bound label particles in step (d) are magnetized by a magnetic field generator and preferably by a wire coil, a straight wire, a conductive microfabricated trace, or a permanent magnet.

32. A method according to claim 20, wherein the unbound label particles are removed by applying a magnetic force to the particles and preferably by an electromagnet, an air-cored coil, or a permanent magnet.

33. A method according to claim 32, wherein the magnetic force is applied by the magnet field generator for magnetizing the label particles.

34. A method according to claim 20, wherein the binding molecules are antibodies; poly- or oligo- nucleotides, i.e. DNA or RNA; proteins; synthetic polypeptides; or chelators.

35. A method according to claim 20, wherein the target molecules are selected from the group consisting of polynucleic acids, proteins, metal ions, and low molecular weight organic species such as toxins, illicit drugs, and explosives.

36. A method according to claim 20, wherein the monitoring in step (e) uses a Wheatstone bridge for monitoring both a magnetic field sensor having closely-attached binding elements and an identical field sensor without binding elements.

37. A method according to claim 20, wherein the contacting in step (b) is done by placing said sample in a solution, applying the solution to the detector, then applying a second solution containing one or more species of magnetizable label particles, wherein said particles have attached label-bound binding molecules with a selective binding response to the target molecules, whereby in the presence of said target molecules said label-bound binding molecules and said sensor-bound binding molecules will sandwich said target molecule, thereby forming a link between said magnetizable label particle and said sensor.

* * * * *